United States Patent
Tweden et al.

[11] Patent Number: 6,102,941
[45] Date of Patent: Aug. 15, 2000

[54] TRANSMYOCARDIAL IMPLANT WITH CORONARY INGROWTH

[75] Inventors: Katherine S. Tweden, Mahtomedi; Guy P. Vanney, Blaine; Thomas L. Odland, Lino Lakes, all of Minn.

[73] Assignee: HeartStent Corporation, St. Paul, Minn.

[21] Appl. No.: 09/246,596

[22] Filed: Feb. 8, 1999

Related U.S. Application Data

[63] Continuation-in-part of application No. 08/944,313, Oct. 6, 1997, Pat. No. 5,984,956.

[51] Int. Cl.[7] ........................................................ A61F 2/06
[52] U.S. Cl. .................................................................. 623/1
[58] Field of Search ................................ 623/1, 2, 11, 12; 606/108, 191, 194, 195, 198

[56] References Cited

U.S. PATENT DOCUMENTS

| | | |
|---|---|---|
| 4,300,244 | 11/1981 | Bokros . |
| 4,374,669 | 2/1983 | Mac Gregor . |
| 4,400,833 | 8/1983 | Kurland . |
| 4,728,328 | 3/1988 | Hughes et al. . |
| 4,769,029 | 9/1988 | Patel . |
| 4,769,031 | 9/1988 | McGough et al. . |
| 5,078,735 | 1/1992 | Mobin-Uddin . |
| 5,222,980 | 6/1993 | Gealow . |
| 5,254,113 | 10/1993 | Wilk . |
| 5,429,144 | 7/1995 | Wilk . |
| 5,443,497 | 8/1995 | Venbrux . |
| 5,545,217 | 8/1996 | Offray et al. . |
| 5,545,227 | 8/1996 | Davidson et al. . |
| 5,591,226 | 1/1997 | Trerotola et al. . |
| 5,655,548 | 8/1997 | Nelson et al. . |
| 5,755,682 | 5/1998 | Knudson et al. . |
| 5,944,019 | 8/1999 | Knudson et al. ............................ 623/1 |

FOREIGN PATENT DOCUMENTS

| | | |
|---|---|---|
| WO 84/02266 | 6/1984 | WIPO . |
| WO 94/21197 | 9/1994 | WIPO . |
| WO 97/27898 | 8/1997 | WIPO . |
| WO 98/06356 | 2/1998 | WIPO . |
| WO 98/08456 | 3/1998 | WIPO . |
| WO 98/46115 | 10/1998 | WIPO . |
| WO 99/17683 | 4/1999 | WIPO . |

OTHER PUBLICATIONS

Sawyer, P.N. et al., "Electron Microscopy and Physical Chemistry of Healing in Prosthetic Heart Valves, Skirts, and Struts", *The Journal of Thoracic and Cardiovascular Surgery*, vol. 67, No. 1, pp. 24–43 (Jan. 1974).

Schurmann, K., et al., "Iliac Arteries: Plain and Heparin–Coated Dacron–Covered Stent–Grafts Compared with Non-covered Metal Stents—An Experimental Study", *Radiology*, vol. 203, No. 1, pp. 55–63 (Apr. 1997).

U.S. Application Serial No. 08/944,313, filed Oct. 6, 1997.
U.S. Application Serial No. 08/882,397, filed Jun. 25, 1997.

*Primary Examiner*—Michael Buiz
*Assistant Examiner*—Vy Q. Bui
*Attorney, Agent, or Firm*—Merchant & Gould P.C.

[57] ABSTRACT

The transmyocardial implant for establishing blood flow through the myocardium between a heart chamber and a lumen of a coronary vessel includes a hollow rigid conduit extending between the lumen and the heart chamber. The conduit includes a first portion for placement in the vessel. The first portion includes an attachment location spaced from an open end for securing a suture around the vessel overlying the first portion at the attachment location. The conduit is formed of a rigid material to resist deformation in response to contraction of the myocardium and the conduit is resistant to thrombus. A tissue growth-inducing material is secured to an exterior of the first portion at the attachment location.

6 Claims, 1 Drawing Sheet

6,102,941

TRANSMYOCARDIAL IMPLANT WITH CORONARY INGROWTH

CROSS REFERENCE TO RELATED APPLICATION

This application is a continuation-in-part of U.S. patent application Ser. No. 08/944,313 which was filed on Oct. 6, 1997, now U.S. Pat. No. 5,984,956.

BACKGROUND OF THE INVENTION

1. Field of the Invention

This invention pertains to an implant for directing blood flow directly between a chamber of the heart and a coronary vessel. More particularly, this invention pertains to such an implant with an enhanced design for fixating the implant in a coronary vessel.

2. Description of the Prior Art

U.S. Pat. No. 5,755,682 dated May 26, 1998 and PCT Application No. PCT/US97/13980 (International Publication No. WO 98/06356 based on U.S. patent application Ser. No. 08/882,397 filed Jun. 25, 1997) teach an implant for defining a blood flow conduit directly from a chamber of the heart to a lumen of a coronary vessel. An embodiment disclosed in the aforementioned patent and applications teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced patent and applications, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant" teaches an implant such as that shown in the aforementioned '682 patent with an enhanced fixation structure. The enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. When placing a portion of the implant in the coronary vessel, the vessel is axially incised a length sufficient to insert the implant. The implant vessel portion is placed within the vessel.

In a preferred embodiment, the implant is rigid. An artery is flexible. A pulsing and alternating flow of blood through the rigid implant and flexible vessel can result in relative movement between through the implant and vessel. As a result of such movement, a rubbing action may occur with the implant causing cellular and extracellular matrix ("ECM") damage to the vessel. Such damage may stimulate cellular migration and proliferation and ECM changes resulting in a fibrotic and thrombotic response which grows to block the implant or artery. Also, as the artery enlarges due to blood flow, an annular gap may exist around the implant in which stagnant blood may collect and stimulate thrombosis. Also, a smooth titanium implant may slip axially relative to a vessel in which the implant is placed. It is an object of the present invention to provide an implant with a reduced likelihood of such response.

SUMMARY OF THE INVENTION

According to a preferred embodiment of the present invention, a transmyocardial implant is disclosed for establishing blood flow through the myocardium between a heart chamber and a lumen of a coronary vessel. The implant includes a hollow rigid conduit extending between the lumen and the heart chamber. The conduit includes a first portion for placement in the vessel. The first portion includes an attachment location spaced from an open end for securing a suture around the vessel overlying the first portion at the attachment location. The conduit is formed of a rigid material to resist deformation in response to contraction of the myocardium and the conduit is resistant to thrombus. A tissue growth-inducing material is secured to an exterior of the first portion at the attachment location.

DESCRIPTION OF THE PREFERRED EMBODIMENT

Figure 1:
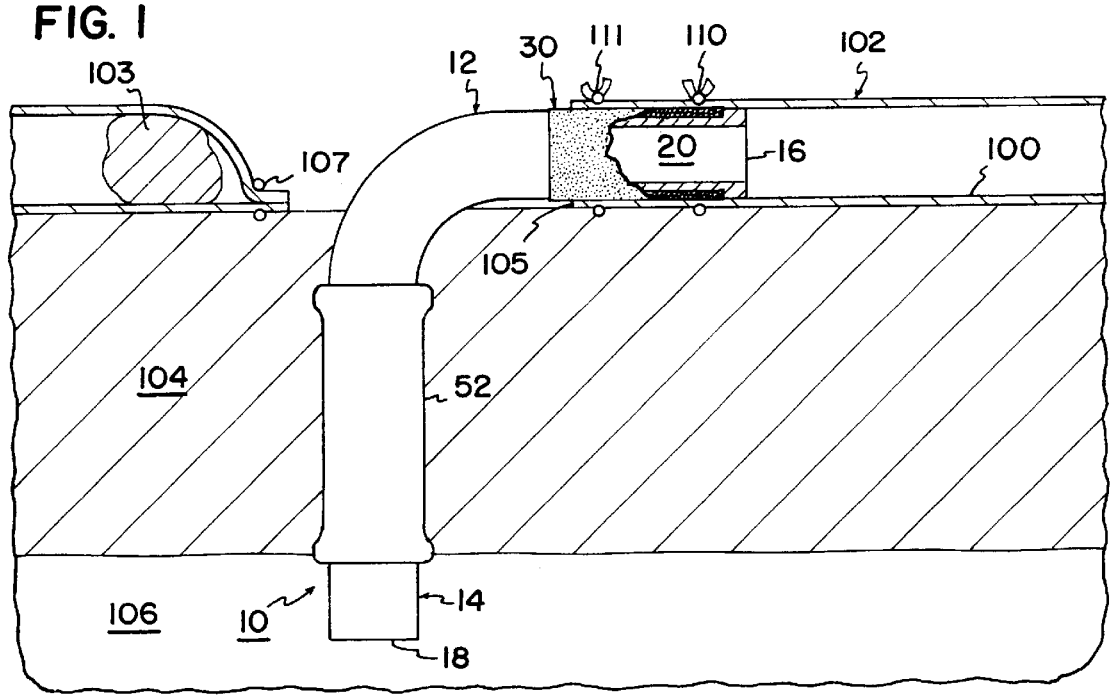
FIG. 1 is a side elevation view of a transmyocardial implant with a vessel ingrowth area, shown partially in section, according to the present invention with the implant in place in a heart wall and in a coronary vessel.

With initial reference to FIG. 1, a conduit 10 is shown in the form of an L-shaped rigid tube. The conduit 10 may be formed of titanium or other rigid biocompatible material such as nickel-titanium alloy or pyrolytic carbon or may be titanium or other material that is coated with pyrolytic carbon. The material of the conduit 10 is preferably a rigid material in order to withstand contraction forces of the myocardium, as will be described. In the preferred embodiment, the tube will have an outside diameter $D_O$ of about 2–3 millimeters and an internal diameter $D_I$ of about 1–2 millimeters to provide a wall thickness of about 0.5 millimeters.

The tube 10 has a first portion 12 sized to be received within the lumen of a coronary vasculature such as the lumen 100 of a coronary artery 102. The conduit 10 has a second portion 14 extending at a right angle to the axis of portion 12. The second portion 14 is sized to extend from the coronary artery 102 directly through a myocardium 104 and protrude into the left ventricle 106 of a patient's heart. The second portion 14 is sized to have a length sufficient for the portion 14 to protrude into the left ventricle 106. By way of example, such a length may be 25 mm.

The first portion 12 has a first opening 16 and the second portion 14 has a second opening 18 in communication with an interior 20 of the implant 10. Therefore, blood can freely flow through the implant 10 between the left ventricle 106 and the lumen 100 of the coronary artery 102.

As mentioned, the tube 10 is preferably formed of titanium or other smooth biocompatible material in order to resist tissue growth and thrombus deposition on the surfaces of the conduit 10. Titanium is a presently preferred material due its long-term use in the cardiovascular industry. Further, titanium is sufficiently rigid to withstand deformation forces caused by contraction of the myocardium 104 to avoid deformation of the tube 10 so that the tube 10 remains open during both diastole and systole.

Since the titanium is resistant to thrombus formation, the titanium of the tube 10 does not attach the device within the myocardium 104 and the lumen 100 of the patient. Therefore, the implant 10 includes a sleeve 52 of tissue growth-inducing material secured to an exterior surface of the conduit 10. In the embodiments of FIG. 1, the sleeve 52 resides exclusively on the second portion 14 in order to reside exclusively within the myocardium 104 after surgical placement of the implant 10.

Preferably, the sleeve 52 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric to anchor the fabric and, hence, the tube 10 to the patient's tissue. As a result, the sleeve 52 is selected to induce tissue attachment.

It is anticipated that tissue growth on and into the sleeve 52 could result in a buildup of tissue beyond the sleeve 52 to a thickness of about 1 millimeter. It is desirable that such tissue growth does not extend over end 18. Accordingly, the lower end of the sleeve 52 is spaced from end 18 by a distance greater than an anticipated thickness of tissue growth extension beyond the sleeve 52. Since the anticipated thickness of tissue growth is about 1 millimeter, the lower end is preferably spaced 1 millimeter from tube end 18. However, a conservative additional spacing of 4–5 millimeters is preferred.

While a fabric tissue growth inducing material is illustrated, other materials could be used. For example, the tissue growth inducing material could be sintered metal on the external surface of the tube 10. Sintered metal results in a porous surface to receive tissue growth. The area of the sintered metal will be spaced from end 18 to prevent tissue accumulation on the sintered area from growing over and blocking end 18.

It will be appreciated the description of a sleeve as described is the subject of commonly assigned and copending U.S. patent application Ser. No. 08/944,313 filed Oct. 6, 1997, entitled "Transmyocardial Implant", and filed in the name of inventors Katherine S. Tweden, Guy P. Vanney and Thomas L. Odland.

When placing the vessel portion 12 in the lumen 100, a length of the artery 102 distal to an obstruction 103 is dissected from the myocardium 104. An incision 105 is formed through the dissected artery 102. Sutures 107 ligate a proximal portion of the artery 102 distal to the obstruction 103. The vessel portion 12 is inserted through the incision 105 into the lumen 100 of a distal portion of the artery 102.

The vessel portion 12 is provided with a tissue ingrowth area 30 adjacent the free end 16. The tissue ingrowth area 30 is spaced about 0.5 mm–1.5 mm (preferably about 0.5 mm) from the free end 16 to avoid tissue growth from migrating into the interior 20 of the implant 10. While the tissue ingrowth area 30 could extend to the free end 16, it is presently anticipated that a short spacing of the area 30 from the free end 16 is desirable.

Figure 2:
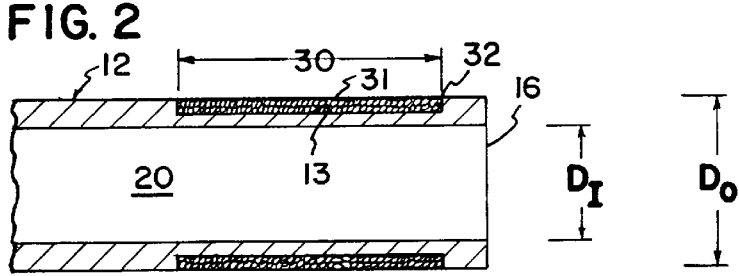
FIG. 2 is a cross-sectional view of a vessel portion of the implant of FIG. 1 with the vessel ingrowth area formed by a sintered metal layer according to one embodiment of the present invention.
Figure 3:
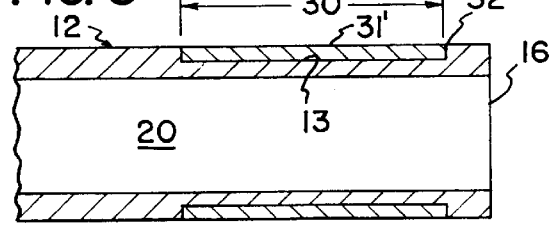
FIG. 3 is the view of FIG. 2 with the vessel ingrowth area formed a fabric layer according to an alternative embodiment of the present invention.
Figure 4:
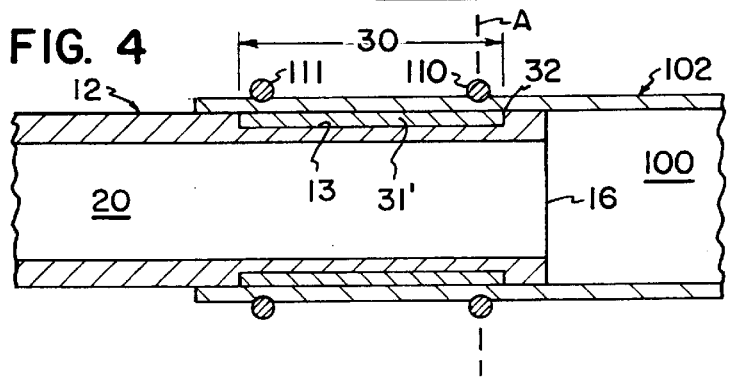
FIG. 4 shows the view of FIG. 3 placed in a vessel and illustrating an attachment location.

The tissue ingrowth area 30 is an annular surface surrounding the exterior of the vessel portion 12. The area 30 permits cellular (e.g., fibroblasts and extra-cellular matrix such as collagen) ingrowth from a vessel (e.g., artery or vein) surrounding the vessel portion 12. The area 30 is provided with a plurality of exposed interstitial spaces to permit such ingrowth. The area 30 may be formed in any one of a number of ways to form such spaces. For example, in the embodiments of FIGS. 1 and 2, the vessel portion 12 may be provided with a wide annular groove 13 terminating 0.5 mm from the free end 16. The groove 13 may be filled with sintered metal 31 such as sintered titanium formed by elevating powder titanium to a sintering temperature. The resulting sintered area 30 is porous to permit ingrowth. In the embodiment of FIG. 2, the groove 13 may be filled with a polyester fabric wrap 31. The fibers of the wrap 31' define the interstitial spaces.

The implant 10 is placed by inserting the vessel portion 12 into the lumen 100. A surgeon then places an attachment device 110, 111 around the vessel 102 and overlying the ingrowth area 30. For example, the attachment device 110, 111 may be a stay suture or clip. Preferably, a suture 110 is placed at an attachment location A near a distal end 32 of the ingrowth area 30. A second suture 111 is placed more proximally.

In use, tissue of the vessel 102 grows into the ingrowth area 30. Such growth prevents relative movement between the vessel 102 and the implant 10. Further, such growth prevents a ballooning of the vessel 102 around the vessel portion 12 precluding the formation of stagnant blood areas between the vessel portion 12 and the vessel 102.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims are appended hereto.

What is claimed:

1. A transmyocardial implant for establishing a blood flow path through a myocardium between a heart chamber and a lumen of a coronary vessel residing on an exterior of said myocardium, said implant comprising:

a hollow rigid conduit having a first portion and a second portion, said first portion sized to be received within said lumen and said second portion sized to extend from said vessel through said myocardium into said chamber, said conduit having open first and second ends on respective ones of said first and second portions to define a blood flow pathway within an interior of said conduit between said first and second ends;

said conduit formed of a conduit material sufficiently rigid to resist deformation and closure of said pathway in response to contraction of said myocardium and said conduit material resistant to thrombus formation;

a first tissue growth inducing material secured to an exterior of said second portion for ingrowth of said myocardium into said first tissue growth inducing material;

a second tissue growth inducing material secured to an exterior of said first portion for ingrowth of said vessel into said second tissue growth inducing material; and said first portion including an attachment location overlying said second tissue growth inducing material for securing a suture around said vessel overlying said first portion at said attachment location.

2. A transmyocardial implant according to claim 1 wherein said first and second tissue growth inducing material is spaced from said first and second ends a distance to avoid tissue growth on said tissue growth inducing material from extending over and blocking said first and second ends.

3. A transmyocardial implant according to claim 1 wherein said second tissue growth inducing material includes a plurality of fibers defining a plurality of interstitial spaces for receiving tissue growth and said tissue growth inducing material is biocompatible.

4. A transmyocardial implant according to claim 3 wherein said second tissue growth inducing material is a polyester fabric.

5. A transmyocardial implant according to claim 1 wherein said second tissue growth inducing material includes a porous layer on said exterior of said conduit.

6. A transmyocardial implant according to claim 5 wherein said porous layer is a sintered material.

* * * * *